US012642552B2

(12) United States Patent (10) Patent No.: US 12,642,552 B2
Xia et al. (45) Date of Patent: Jun. 2, 2026

(54) CIRCUMCISION EQUIPMENT

(71) Applicant: Wuhu ShangRing Technology Co., Ltd, Wuhu (CN)

(72) Inventors: Shujie Xia, Shanghai (CN); Huarong Yu, Beijing (CN); Jingjing Shang, Wuhu (CN); Jianzhong Shang, Wuhu (CN)

(73) Assignee: Wuhu ShangRing Technology Co., Ltd, Wuhu (CN)

( * ) Notice: Subject to any disclaimer, the term of this patent is extended or adjusted under 35 U.S.C. 154(b) by 102 days.

(21) Appl. No.: 18/625,195

(22) Filed: Apr. 2, 2024

(65) Prior Publication Data

US 2024/0245430 A1 Jul. 25, 2024

Related U.S. Application Data

(60) Division of application No. 16/531,139, filed on Aug. 5, 2019, now Pat. No. 11,980,390, which is a
(Continued)

(30) Foreign Application Priority Data

| | | | |
|---|---|---|---|
| Feb. 4, 2017 | (CN) | ......................... | 201710063339.X |
| Feb. 4, 2017 | (CN) | ......................... | 201710063340.2 |
| Feb. 4, 2017 | (CN) | ......................... | 201710065136.4 |
| Feb. 4, 2017 | (CN) | ......................... | 201710065137.9 |
| Feb. 4, 2017 | (CN) | ......................... | 201710065138.3 |
| Feb. 4, 2017 | (CN) | ......................... | 201710065139.8 |
| Feb. 4, 2017 | (CN) | ......................... | 201710065140.0 |
| Feb. 4, 2017 | (CN) | ......................... | 201710065146.8 |
| Feb. 4, 2017 | (CN) | ......................... | 201710065147.2 |
| Feb. 4, 2017 | (CN) | ......................... | 201710065148.7 |
| Feb. 4, 2017 | (CN) | ......................... | 201710065149.1 |
| Feb. 4, 2017 | (CN) | ......................... | 201710065150.4 |
| Feb. 4, 2017 | (CN) | ......................... | 201720109034.3 |
| Apr. 18, 2017 | (CN) | ......................... | 201710250780.9 |
| Apr. 18, 2017 | (CN) | ......................... | 201710250951.8 |
| Apr. 19, 2017 | (CN) | ......................... | 201710254989.2 |
| Apr. 19, 2017 | (CN) | ......................... | 201710255021.1 |
| Apr. 19, 2017 | (CN) | ......................... | 201710255023.0 |

(Continued)

(51) Int. Cl.
*A61B 17/326* (2006.01)
*A61B 17/068* (2006.01)
(Continued)

(52) U.S. Cl.
CPC ........ *A61B 17/326* (2013.01); *A61B 17/0682* (2013.01); *A61B 17/072* (2013.01);
(Continued)

(58) Field of Classification Search
CPC .............. A61B 17/326; A61B 17/0682; A61B 17/1155
See application file for complete search history.

(56) References Cited

FOREIGN PATENT DOCUMENTS

| | | | |
|---|---|---|---|
| CN | 204890072 | * | 12/2015 |
| CN | 106214224 | * | 12/2016 |

* cited by examiner

*Primary Examiner* — Thomas Mcevoy
(74) *Attorney, Agent, or Firm* — JEEN IP LAW, LLC

(57) ABSTRACT

The present invention relates to surgical devices, particularly to a circumcision apparatus, enable the circumcision apparatus to be suitable for different surgery objects and environments.

9 Claims, 5 Drawing Sheets

Related U.S. Application Data continuation of application No. PCT/CN2018/074988, filed on Feb. 1, 2018.

(30)     Foreign Application Priority Data

| | | |
|---|---|---|
| Apr. 19, 2017 | (CN) | ......................... 201710255025.X |
| Apr. 24, 2017 | (CN) | ......................... 201710273894.5 |
| Apr. 24, 2017 | (CN) | ......................... 201710273895.X |
| Apr. 24, 2017 | (CN) | ......................... 201710274306.X |
| Apr. 24, 2017 | (CN) | ......................... 201710274307.4 |
| Apr. 24, 2017 | (CN) | ......................... 201710274308.9 |
| Apr. 24, 2017 | (CN) | ......................... 201710274309.3 |
| Apr. 24, 2017 | (CN) | ......................... 201710274396.2 |
| Apr. 24, 2017 | (CN) | ......................... 201710274397.7 |
| Apr. 24, 2017 | (CN) | ......................... 201710274398.1 |
| Apr. 24, 2017 | (CN) | ......................... 201710274399.6 |
| Apr. 24, 2017 | (CN) | ......................... 201710274400.5 |
| Apr. 24, 2017 | (CN) | ......................... 201710274426.X |
| Aug. 18, 2017 | (CN) | ......................... 201710709597.0 |

(51) Int. Cl.
| | |
|---|---|
| *A61B 17/072* | (2006.01) |
| *A61B 17/115* | (2006.01) |
| *A61B 90/00* | (2016.01) |
| *A61B 17/00* | (2006.01) |

(52) U.S. Cl.
CPC .......... *A61B 17/1155* (2013.01); *A61B 90/08* (2016.02); *A61B 2017/00561* (2013.01); *A61B 2017/07228* (2013.01); *A61B 2017/07285* (2013.01); *A61B 2090/0811* (2016.02)

11-1

4-3

CIRCUMCISION EQUIPMENT

CROSS REFERENCE TO RELATED APPLICATIONS

The present application is a Divisional Application of U.S. patent application Ser. No. 16/531,139 filed on Aug. 5, 2019, which is a Continuation Application of PCT Application No. PCT/CN2018/074988 filed on Feb. 1, 2018, which claims the benefit of Chinese patents application Nos. 201710063339.X, 201710065146.8, 201710065140.0, 201710065139.8, 201710065138.3, 201710065150.4, 201710065149.1, 201710065148.7, 201710065147.2, 201710063340.2, 201710065137.9, 201710065136.4, 201720109034.3 filed on Feb. 4, 2017, Chinese Patent Application Nos. 201710250780.9 and 201710250951.8 filed on Apr. 18, 2017, Chinese Patent Application Nos. 201710254989.2, 201710255021.1, 201710255023.0 and 201710255025.X filed on Apr. 19, 2017, Chinese patents application Nos. 201710274426.X, 201710274400.5, 201710274399.6, 201710274398.1, 201710274397.7, 201710274396.2, 201710274309.3, 201710274308.9, 201710274307.4, 201710274306.X, 201710273895.X and 201710273894.5 filed on Apr. 24, 2017, and Chinese Patent Application No. 201710709597.0 filed on Aug. 18, 2017. All the above are hereby incorporated by reference.

FIELD OF THE INVENTION

The present invention relates to surgical devices, particularly to a circumcision apparatus and more particularly to a B-type valgus circumcision stapler.

BACKGROUND OF THE INVENTION

Refer to the B-type valgus circumcision stapler. The redundant prepuce or phimosis is one of the causes of male urinary system infections and sexually transmitted diseases. The redundant prepuce or phimosis can cause urinary tract infections, resulting in chronic prostatitis, with a series of symptoms, such as pains in back and waist, impotence and premature ejaculation. Therefore, the removal of the redundant prepuce is a good way to prevent these diseases.

Traditionally, surgical removal of the phimosis or redundant prepuce has the main technical points of removal of excess prepuce, hemostasis, and apposition suture of cut edges to skin. A postoperative patient cannot move around, suffers unbearable pain in each change of ointment and endures huge pain when stitches are taken out finally. In addition, incomplete ligating hemostasis will cause prepuce hematoma, thus requiring a surgical treatment again. Furthermore, since the prepuce removal and the hemostasis processes are performed separately, the surgery time is prolonged, and the patient's panic is exacerbated.

A therapeutic method of applying a laser and high-frequency electric surgical knife technology to circumcision has been developed at present. Although this therapeutic method substitutes for scissors cutting and makes a bleeding spot coagulated, the patient's tissues will be burnt and susceptible to infection.

Then, a circumcision device was developed in this field. In the circumcision device, a prepuce incision is sutured using a suturing nail in one step. However, during a surgery using a conventional built-in circumcision stapler in the prior art, a front prepuce and most of a penis are exposed outside, so that the prepuce and the penis are vulnerable to injury or infection. A portion above a prepuce clamping portion of the built-in circumcision stapler is located outside the circumcision stapler, while a U-nail suturing position is located at the top of the circumcision stapler. Once hemorrhage caused by instrument failure or misoperation occurs, a patient is likely to be infected to cause a surgical accident. The built-in circumcision stapler has a built-in circumcision knife, and thus carries out cutting inside and nailing at periphery. In case of a redundant prepuce or the like, the possibility of cutting of overlapped tissues is high, causing pain and risks. In addition, if circumcision and hemostasis with U-nails are performed as soon as appropriate clamping is realized only through cooperation between an upper cover (upper comprehensive cover) and a lower cover (lower comprehensive cover/connecting cover) as well as between an inner ring (prepuce fixing hoop) and an inner comprehensive cover (U-nail top ring and/or thimble guide block), a prepuce blood vessel cannot be accurately positioned as a built-in nail groove is not visible. As a result, the U-nail in the U-nail groove cannot accurately correspond to the prepuce blood vessel during the surgery, so that a hemostasis effect is poor. Even, the head of the U-nail may be just hammered into the blood vessels, resulting in a surgery risk as hemostasisis not punctual. Moreover, in the existing technology, as the U-nail is directly hammered into the prepuce, the U-nail is likely to adhere with the prepuce and even U-nail cannot peel off punctually as the U-nail deeply penetrates into the prepuce in a process of waiting for necrosis and defluvium of the prepuce and peeling off of the U-nail after the surgery, causing severe pain to the patient.

BRIEF DESCRIPTION OF THE DRAWINGS

Refer to the B-type valgus circumcision stapler.

SPECIFIC DESCRIPTION OF THE EMBODIMENTS

Refer to the B-type valgus circumcision stapler.

The present invention will be described in detail below with reference to the accompanying drawings. The followings show preferred embodiments in various embodiments of the present invention.

Figure 1:
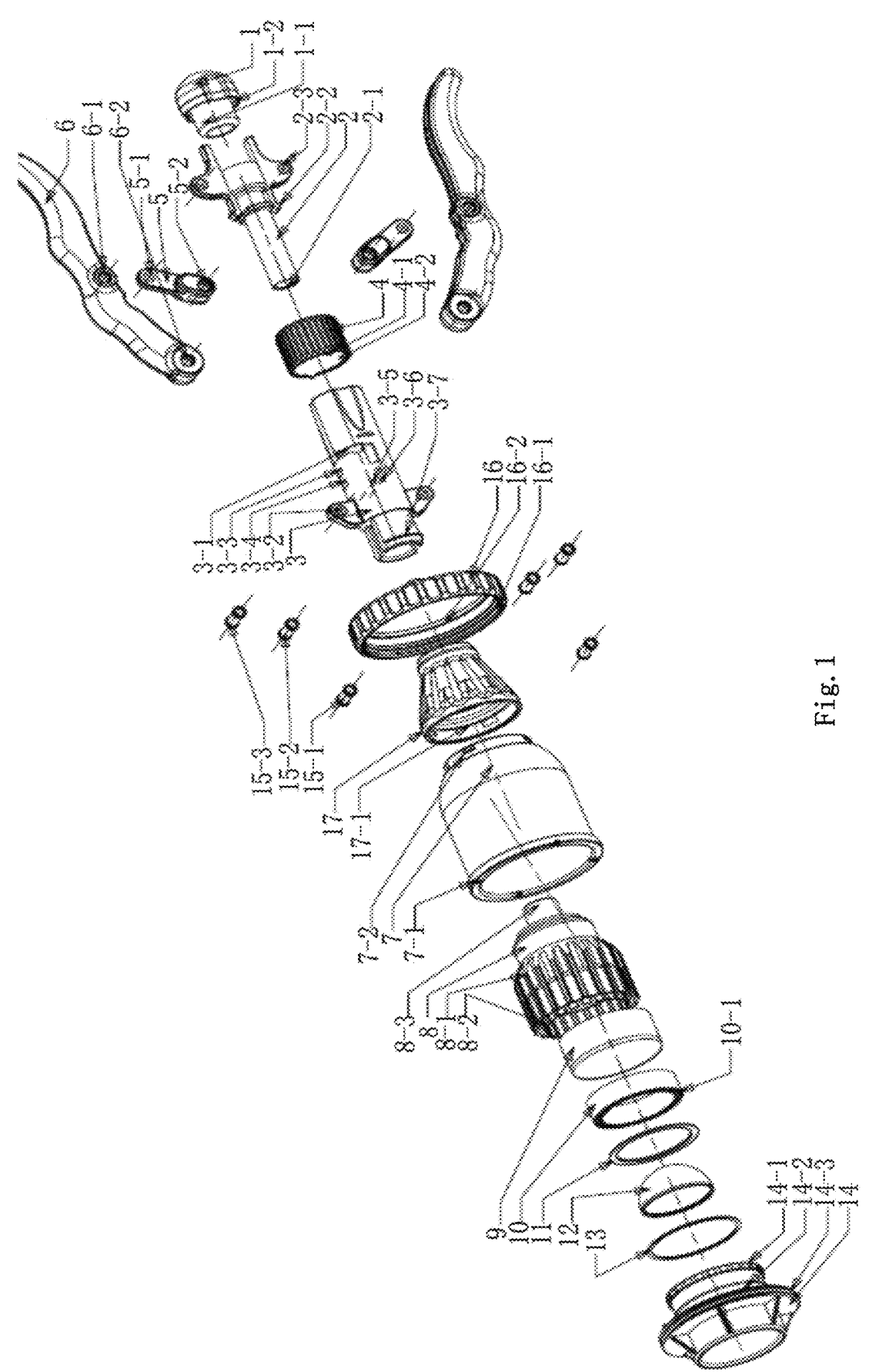
FIG. 1 is an exploded view of a valgus circumcision stapler.
Figure 2:
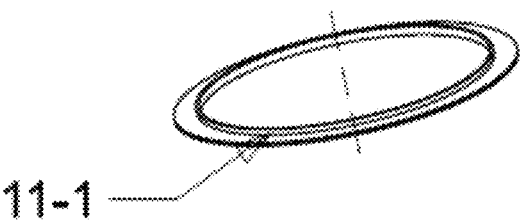
FIG. 2 is an enlarged view of a U-nail gasket.
Figure 3:
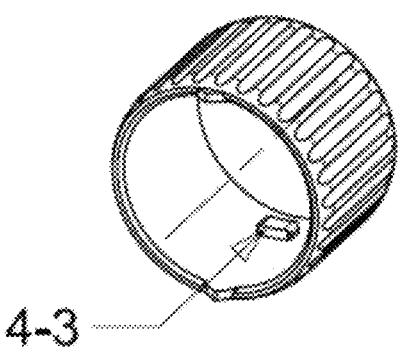
FIG. 3 is an enlarged view of an opening knob.

FIGS. 1-3 are exploded views of a valgus circumcision stapler. The valgus circumcision stapler includes a plug 1, a circular stage 1-1, a groove 1-2, a push rod 2, a convex stage 2-1, a first hook 2-2, a first pin hole 2-3, a connecting block 3, a guide groove 3-1, a second pin hole 3-2, a first hanging stage 3-3, a second hanging stage 3-4, a closing indicator 3-5, an opening indicator 3-6, a second hook 3-7, an opening knob 4, a pointer 4-1, a middle circular hole 4-2, a guide block 4-3, a small connecting rod 5, a third pin hole 5-1, a fourth pin hole 5-2, a handle 6, a fifth pin hole 6-1, a sixth pin hole 6-2, a lower comprehensive cover 7, a hanging stage 7-1, a hook 7-2, a U-nail top ring 8, a thimble 8-1, a positioning nail 8-2, a lower convex stage 8-3, a circumcision knife 9, a thimble guide block 10, a thimble guide groove 10-1, a U-nail gasket 11, a gasket positioning stage 11-1, a glans protection cover 12, a blade gasket 13, an upper comprehensive cover 14, a blood vessel docking groove 14-1, a positioning hole 14-2, a thread 14-3, a first pin 15-1, a second pin 15-2, a third pin 15-3, a locking ring 16, a thread 16-1, a clamping ring 16-2, a connecting cover 17 and a connecting hook 17-1. The valgus circumcision stapler includes an upper comprehensive cover 14, a lower comprehensive cover 7, the connecting cover 17 and a U-nail device. The upper comprehensive cover 14 and the lower comprehensive cover 7 are releasably connected in a matching manner. A prepuce fixing hoop integrally formed with the upper comprehensive cover 14 is arranged at the lower portion of the upper comprehensive cover 14, or the prepuce fixing hoop is accommodated in the upper comprehensive cover 14. A part or all of the U-nail device is placed in the lower comprehensive cover 7. The upper comprehensive cover 14, the lower comprehensive cover 7 and the U-nail device cooperate to position a penis and/or glans and/or prepuce, and to clamp and/or squeeze and/or cut the prepuce. The connecting cover 17 is connected to the lower portion of the lower comprehensive cover 7.

The U-nail device comprises the U-nail top ring 8 and the thimble guide block 10. The thimble guide block 10 is configured to accommodate a suturing U-nail and/or to guide the movement of the suturing U-nail and/or to position and/or guide the thimble 8-1 of the U-nail top ring 8. The U-nail top ring 8 is configured to cooperate with the thimble guide block 10 to eject the U-nail in the thimble guide block.

The B-type valgus circumcision stapler further comprises the U-nail gasket 11 which is an annular gasket arranged at the top end of the thimble guide block 10.

The U-nail gasket 11 further comprises a gasket positioning stage 11-1 perpendicular to and/or at an angle to the plane of the U-nail gasket 11. The gasket positioning stage 11-1 is one or more protrusions and/or an integral annular protrusion arranged at the inner circumference and/or the outer circumference and/or the middle of the plane of the U-nail gasket 11.

A first through hole is formed in the middle of the thimble guide block 10. The thimble guide block 10 comprises an annular inner wall and/or an annular outer wall and/or a positioning stage accommodating groove. The annular inner wall is configured to cooperate with the one or more protrusions and/or integral annular protrusion arranged at the inner circumference of the plane of the U-nail gasket 11 for positioning; and/or, the annular outer wall is configured to cooperate with the one or more protrusions and/or integral annular protrusion arranged at the outer circumference of the plane of the U-nail gasket 11 for positioning; and/or, the positioning stage accommodating groove is formed at the top end of the thimble guide block 10, and is configured to accommodate the one or more protrusions and/or integral annular protrusion at the middle of the plane of the U-nail gasket 11.

The thimble guide block 10 is provided with a plurality of thimble guide grooves 10-1 annularly formed in the annular thimble guide block 10. The U-nail gasket 11 partially or completely covers the thimble guide grooves 10-1.

One or more positioning nails 8-2 are arranged at the upper end of the U-nail top ring 8, and are configured to cooperate with a positioning hole 14-2 formed in the upper comprehensive cover 14 for positioning; and/or, the U-nail top ring 8 is provided with a plurality of thimbles 8-1 which is in one-to-one correspondence with the plurality of thimble guide grooves 10-1 formed on the thimble guide block 10 and which is configured to eject the suturing U-nail accommodated in each thimble guide groove; and/or, the lower convex stage 8-3 is arranged at the lower end of the U-nail top ring 8, and is configured to position the U-nail top ring in the connecting cover 17 and/or the connecting block 3 below the connecting cover 17.

A second through hole is formed in the middle of the upper comprehensive cover 14, and is configured to allow a penis and/or prepuce and/or glans to pass through; and/or, the prepuce fixing hoop is capable of being positioned in the upper comprehensive cover 14 and cooperates with the upper comprehensive cover 14 to clamp the prepuce, and/or the lower end of the prepuce fixing hoop is capable of cooperating with the U-nail device to clamp the prepuce; and/or, blood vessel docking grooves 14-1, or graduations, or concave/convex points, or concave/convex lines are annularly arranged on the outer surface of the lower end of the upper comprehensive cover 14 and/or the outer surface of a blood vessel fixing hoop, and are in one-to-one correspondence with the thimble guide grooves 10-1, or intervals among the thimble guide grooves 10-1, or the U-nails in the thimble guide grooves 10-1; or, intervals among the blood vessel docking grooves 14-1, or the graduations, or the concave/convex points, or the concave/convex lines are in one-to-one correspondence with the thimble guide grooves 10-1, or the intervals among the thimble guide grooves 10-1, or the U-nails in the thimble guide grooves 10-1; or, a width of every two bulges and/or recesses of the blood vessel docking grooves 14-1, or the graduations, or the concave/convex points or the concave/convex lines is equal to or slightly less than the width of each thimble guide groove 10-1, and/or the width of the U-nail in the corresponding thimble guide groove 10-1, and/or the width of the interval between the thimble guide grooves 10-1.

The B-type valgus circumcision stapler further comprises the glans protection cove 12, and/or the locking ring 16 and/or the circumcision knife 9. The internal thread 16-1/clamping ring 16-2/hanging stage is arranged on the inner ring surface of the locking ring; and/or, the external thread/clamping ring/hanging stage 14-3 is arranged on the outer surface of the upper comprehensive cover 14, and/or an external thread/clamping ring/hanging stage 7-1 is arranged on the outer surface of the lower comprehensive cover 7. The internal thread/clamping ring/hanging stage and the external thread/clamping ring/hanging stage cooperate with each other to position the upper comprehensive cover 14, the lower comprehensive cover 7 and/or the locking ring 16; and/or, the circumcision knife 9 is annularly arranged at the outer circumference of the thimble guide block 10, and is configured to cooperate with the lower end surface of the upper comprehensive cover 14 to cut the prepuce; and/or, the glans protection cover 12 is configured to accommodate and protect the glans, is releasably arranged in the first through hole of the thimble guide block 10, and upwardly corresponds to the second through hole of the upper comprehensive cover 14.

The B-type valgus circumcision stapler further comprises the connecting block 3, the upper end of the connecting block 3 being connected to the lower end of the comprehensive cover; and/or, the blade gasket 13 arranged on the lower end surface of the upper comprehensive cover 14 and corresponding to the circumcision knife 9; and/or, the push rod 2, the upper end of the push rod 2 being inserted into the lower end of the connecting block 3; and/or, the plug 1 arranged at the lower end of the push rod 2; and/or, the handle 6 which is drivingly connected to the connecting block 3 and/or push rod 2, and configured to drive the push rod 2, and/or the connecting block 3, and/or an internal transmission member of the push rod 2 and/or an internal transmission member of the connecting block 3 so as to drive the U-nail device and/or the circumcision knife 9 to move upward; and/or, the opening knob 4 which sleeves the connecting block 3, and is configured to lock or unlock the handle 6 and/or a component driven by the handle 6.

The hook 7-2 is arranged at the lower end of the lower comprehensive cover 7. The connecting hook 17-1 is arranged at the upper end of the connecting cover 17. The hook 7-2 and the connecting hook 17-1 cooperate with each other to connect the lower comprehensive cover 7 and the connecting cover 17.

Figure 4:
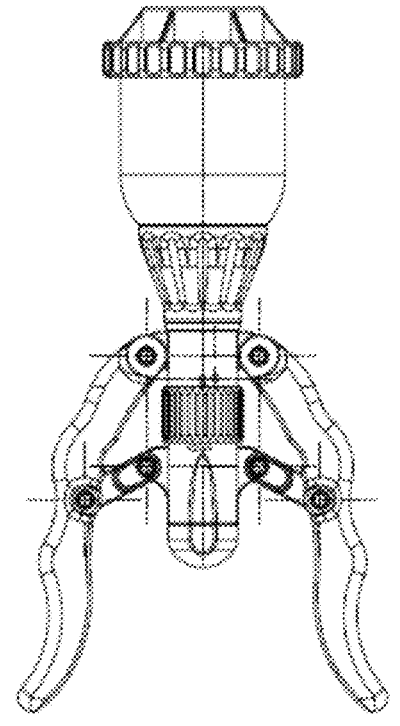
FIG. 4 is a front view of the valgus circumcision stapler.
Figure 5:
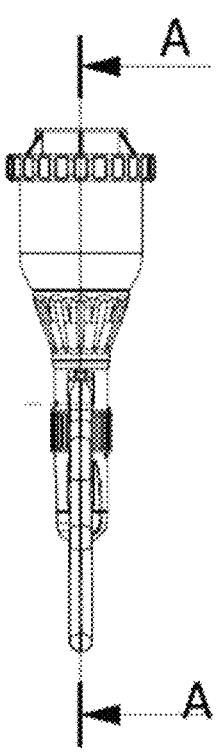
FIG. 5 is a side view of the valgus circumcision stapler.
Figure 6:
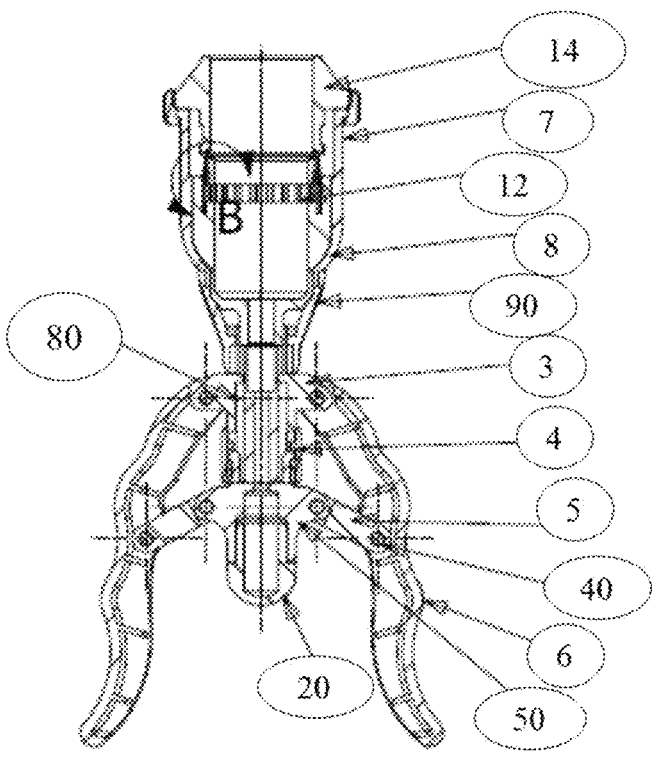
FIG. 6 is a structural view of the valgus circumcision stapler.
Figure 7:
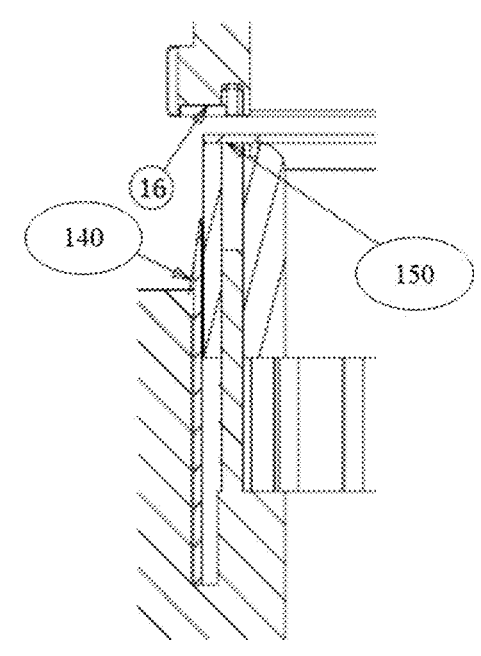
FIG. 7 is an enlarged view of the portion B shown in FIG. 6.
Figure 8:
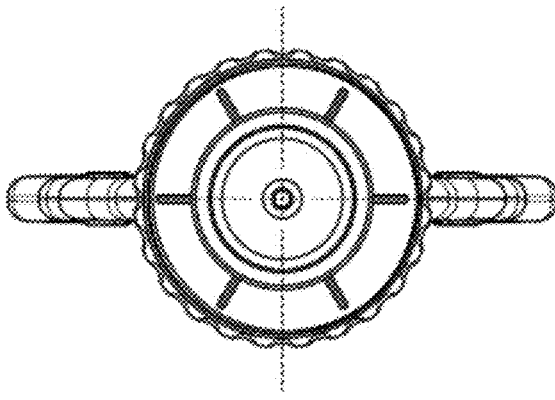
FIG. 8 is a top view of the valgus circumcision stapler.
Figure 9:
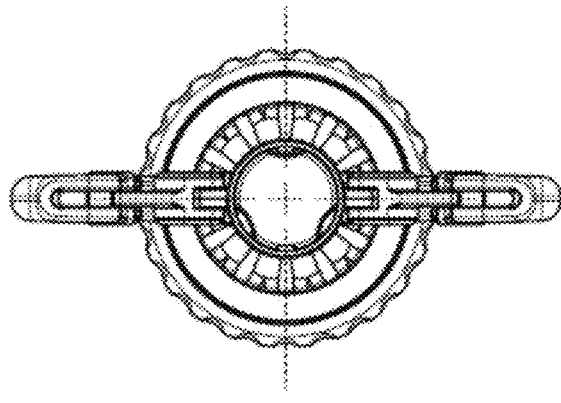
FIG. 9 is a bottom view of the valgus circumcision stapler.
Figure 10:
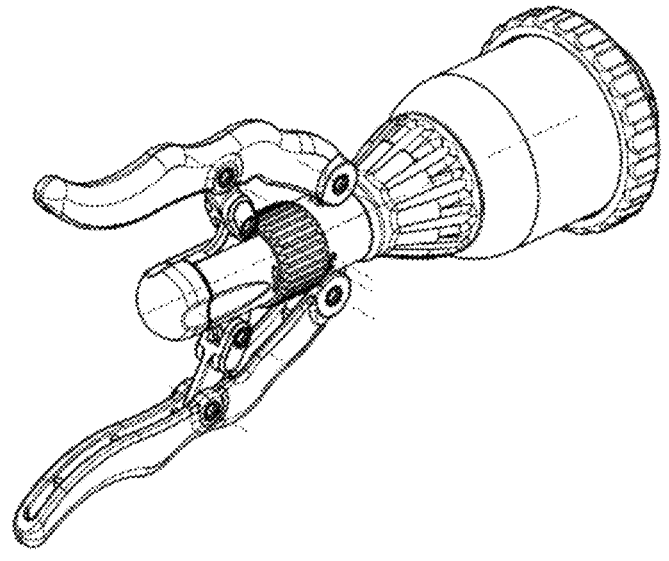
FIG. 10 is a perspective view of the valgus circumcision stapler.

FIG. 4 is a front view of the valgus circumcision stapler. In order to describe the specific structure of the valgus circumcision stapler more clearly according to the drawings, FIGS. 5 and 8-10 are views of the valgus circumcision stapler from all visual angles. Referring to FIGS. 6 and 7, in the preferred embodiment, the valgus circumcision stapler includes a handle 6, a blanking cap 20, a small connecting rod 5, a pin 40, a sliding rod 50, a connecting block 3, an opening knob 4, a spring 80, a connecting cover 90, a U-nail top ring 8, an upper comprehensive cover 14, a lower comprehensive cover 7, a glans protection cover 12, a blade 140, a U-nail washer 15 and a circumcision knife gasket 160.

The handle 6 is drivingly connected to the sliding rod 50 and the connecting block 3 through the small connecting rod 5 and the pin 40. The opening knob 4 sleeves the connecting block 3. The blanking cap 20 is arranged at the lower end of the sliding rod 50. The upper comprehensive cover 14 and the lower comprehensive cover 7 are directly connected or connected through a threaded locking ring. The spring 80 is arranged in the inner cavity of the connecting block 3. A part or all of the U-nail top ring 8 is arranged in the lower comprehensive cover 7. The threaded locking ring locks the peripheries of the upper comprehensive cover 14 and the lower comprehensive cover 7. The circumcision blade 140 is arranged at the periphery of the U-nail top ring 8 and the guide block. The U-nail washer 15 is fixed at the top end of a U-nail groove, so that the U-nail preferably penetrates through the U-nail washer 15 to avoid contact between one or more surfaces of the U-nail and a prepuce tissue when the U-nail is hammered into the prepuce. The glans protection cover 12 is arranged in the thimble guide block and is configured to accommodate and protect the glans. The circumcision knife gasket 160 is arranged on the lower end surface of the upper comprehensive cover and is corresponding to the circumcision knife. The principles of other related driving components, actuating components and circumcision components are the same as those in the previous embodiment, and are not repeated herein.

The above description of the present invention has been given by way of example with reference to the accompanying drawings. It is obvious that the specific implementation of the present invention is not limited to the above modes, and various improvements made using the method concepts and technical solutions of the present invention or directly applied to other occasions, are within the scope of the present invention.

The invention claimed is:

1. A B-type valgus circumcision stapler, comprising: an upper comprehensive cover, a lower comprehensive cover, a U-nail device, and a connecting cover, wherein the upper comprehensive cover and the lower comprehensive cover are releasably connected in a matching manner;

a prepuce fixing hoop integrally formed with the upper comprehensive cover is arranged at the lower portion of the upper comprehensive cover, or the prepuce fixing hoop is accommodated in the upper comprehensive cover;

a part or all of the U-nail device is placed in the lower comprehensive cover;

the upper comprehensive cover, the lower comprehensive cover and the U-nail device cooperate to position a penis and/or glans and/or prepuce, and to clamp and/or squeeze and/or cut the prepuce;

the connecting cover is connected to the lower portion of the lower comprehensive cover;

wherein the U-nail device comprises a U-nail top ring and a thimble guide block; and the B-type valgus circumcision stapler further comprises a U-nail gasket which is an annular gasket arranged at a top end of the thimble guide block.

2. The B-type valgus circumcision stapler of claim 1, wherein the thimble guide block is configured to accommodate a suturing U-nail and/or to guide the movement of the suturing U-nail and/or to position and/or guide a thimble of the U-nail top ring; and the U-nail top ring is configured to cooperate with the thimble guide block to eject the U-nail in the thimble guide block.

3. The B-type valgus circumcision stapler of claim 1, wherein the U-nail gasket further comprises a gasket positioning stage perpendicular to and/or at an angle to the plane of the U-nail gasket; and the gasket positioning stage is one or more protrusions and/or an integral annular protrusion arranged at the inner circumference and/or the outer circumference and/or the middle of the plane of the U-nail gasket.

4. The B-type valgus circumcision stapler of claim 3, wherein a first through hole is formed in the middle of the thimble guide block; the thimble guide block comprises an annular inner wall and/or an annular outer wall and/or a positioning stage accommodating groove; the annular inner wall is configured to cooperate with the one or more protrusions and/or integral annular protrusion arranged at the inner circumference of the plane of the U-nail gasket for positioning; and/or, the annular outer wall is configured to cooperate with the one or more protrusions and/or integral annular protrusion arranged at the outer circumference of the plane of the U-nail gasket for positioning; and/or, the positioning stage accommodating groove is formed at the top end of the thimble guide block, and is configured to accommodate the one or more protrusions and/or integral annular protrusion at the middle of the plane of the U-nail gasket.

5. The B-type valgus circumcision stapler of claim 1, wherein the thimble guide block is provided with a plurality of thimble guide grooves annularly formed in the annular thimble guide block; and the U-nail gasket partially or completely covers the thimble guide grooves.

6. The B-type valgus circumcision stapler of claim 5, wherein one or more positioning nails are arranged at the upper end of the U-nail top ring, and are configured to cooperate with a positioning hole formed in the upper comprehensive cover for positioning; and/or, the U-nail top ring is provided with a plurality of thimbles which is in one-to-one correspondence with the plurality of thimble guide grooves formed on the thimble guide block and which is configured to eject the suturing U-nail accommodated in each thimble guide groove; and/or, a lower convex stage is arranged at the lower end of the U-nail top ring, and is configured to position the U-nail top ring in the connecting cover or a connecting block below the connecting cover.

7. The B-type valgus circumcision stapler of claim 1, wherein a second through hole is formed in a middle of the upper comprehensive cover, and is configured to allow a penis and/or prepuce and/or glans to pass through; and/or, the prepuce fixing hoop is capable of being positioned in the upper comprehensive cover and cooperates with the upper comprehensive cover to clamp the prepuce, and/ or the lower end of the prepuce fixing hoop is capable of cooperating with the U-nail device to clamp the prepuce;

and/or, blood vessel docking grooves, or graduations, or concave/ convex points, or concave/convex lines are annularly arranged on an outer surface of the lower end of the upper comprehensive cover and/or an outer surface of a blood vessel fixing hoop, and are in one-to-one correspondence with thimble guide grooves, or intervals among thimble guide grooves, or U-nails in thimble guide grooves; or, intervals among the blood vessel docking grooves, or the graduations, or the concave/convex points, or the concave/convex lines are in one-to-one correspondence with the thimble guide grooves, or the intervals among the thimble guide grooves, or the U-nails in the thimble guide grooves; or, a width of bulges and/or recesses of the blood vessel docking grooves, or the graduations, or the concave/ convex points or the concave/convex lines is equal to or slightly less than the width of each thimble guide groove, and/or the width of the U-nail in the corresponding thimble guide groove, and/or the width of the interval between the thimble guide grooves.

8. The B-type valgus circumcision stapler of claim 1, further comprising a glans protection cover, and/or a locking ring, and/or a circumcision knife, wherein an internal thread/clamping ring/hanging stage is arranged on the inner ring surface of the locking ring; an external thread/clamping ring/hanging stage is arranged on the outer surface of the upper comprehensive cover, and/or is arranged on the outer surface of the lower comprehensive cover, and the internal thread/ clamping ring/hanging stage and the external thread/ clamping ring/hanging stage cooperate with each other to position the upper comprehensive cover, the lower comprehensive cover and/or the locking ring;

and/or, the circumcision knife is annularly arranged at the outer circumference of the thimble guide block, and is configured to cooperate with the lower end surface of the upper comprehensive cover to cut the prepuce;

and/or, the glans protective cover is configured to accommodate and protect the glans, is releasably arranged in a first through hole of the thimble guide block, and upwardly corresponds to a second through hole of the upper comprehensive cover.

9. The B-type valgus circumcision stapler of claim 8, wherein a hook is arranged at the lower end of the lower comprehensive cover, a connecting hook is arranged at the upper end of the connecting cover, and the hook and the connecting hook cooperate with each other to connect the lower comprehensive cover and the connecting cover;

and/or, the B-type valgus circumcision stapler further comprises a connecting block, the upper end of the connecting block being connected to the lower end of the comprehensive cover;

and/or, the B-type valgus circumcision stapler further comprises a blade gasket arranged on the lower end surface of the upper comprehensive cover and corresponding to the circumcision knife;

and/or, the B-type valgus circumcision stapler further comprises a push rod, the upper end of the push rod being inserted into the lower end of the connecting block;

and/or, the B-type valgus circumcision stapler further comprises a plug arranged at the lower end of the pushing rod;

and/or, the B-type valgus circumcision stapler further comprises a handle which is drivingly connected to the connecting block and/or push rod, and configured to drive the push rod, and/or the connecting block, and/or an internal transmission member of the push rod and/or an internal transmission member of the connecting block so as to drive the U-nail device and/or the circumcision knife to move upward;

and/or, the B-type valgus circumcision stapler further comprises an opening knob which sleeves the connecting block, and is configured to lock or unlock the handle and/or a component driven by the handle.

* * * * *